United States Patent
Matsukata et al.

(10) Patent No.: US 9,645,069 B2
(45) Date of Patent: May 9, 2017

(54) ADSORPTION CHARACTERISTIC MEASURING APPARATUS

(71) Applicants: Waseda University, Tokyo (JP); MicrotracBEL Corporation, Osaka (JP)

(72) Inventors: Masahiko Matsukata, Tokyo (JP); Kazuyuki Nakai, Osaka (JP); Masayuki Yoshida, Osaka (JP)

(73) Assignees: Waseda University, Tokyo (JP); MicrotracBEL Corp., Osaka (JP)

( * ) Notice: Subject to any disclaimer, the term of this patent is extended or adjusted under 35 U.S.C. 154(b) by 0 days.

(21) Appl. No.: 14/853,476

(22) Filed: Sep. 14, 2015

(65) Prior Publication Data
US 2016/0076988 A1 Mar. 17, 2016

(30) Foreign Application Priority Data
Sep. 16, 2014 (JP) .................................. 2014-188290

(51) Int. Cl.
*G01N 15/08* (2006.01)
(52) U.S. Cl.
CPC ... *G01N 15/088* (2013.01); *G01N 2015/0866* (2013.01)

(58) Field of Classification Search
CPC ..................... G01N 15/088; G01N 2015/0866
See application file for complete search history.

(56) References Cited

U.S. PATENT DOCUMENTS 6,595,036 B1 * 7/2003 Nakai ................ G01N 15/0893
422/69

FOREIGN PATENT DOCUMENTS

| JP | 2008-247702 A | 10/2008 |
| JP | 2014-081250 A | 5/2014 |

* cited by examiner

*Primary Examiner* — Hezron E Williams
*Assistant Examiner* — David Z Huang
(74) *Attorney, Agent, or Firm* — Dorsey & Whitney LLP (57) ABSTRACT

An adsorption characteristic measuring apparatus according to the invention supplies a predetermined adsorption gas to a film formed body as a sample accommodated in a sample tube to measure adsorption characteristics. In the inside of the sample tube, a void between an inner wall surface of the sample tube and the sample is filled with a particle-like filler having higher thermal conductivity than the adsorption gas under a measurement pressure. In addition, a glass rod as a dead volume reducing rod, a spacer ring for forming a thermal insulation space between the particle-like filler and the glass rod, and a reflective plate for reflecting radiant heat are disposed.

7 Claims, 3 Drawing Sheets

ADSORPTION CHARACTERISTIC MEASURING APPARATUS

CROSS-REFERENCE TO RELATED APPLICATION(S)

This application claims priority to Japanese Patent Application No. 2014-188290, filed on Sep. 16, 2014, the entire disclosure of which is incorporated herein by reference.

BACKGROUND

Technical Field

The present invention relates to an adsorption characteristic measuring apparatus, and more particularly to an adsorption characteristic measuring apparatus for obtaining an adsorption isotherm using a constant volume method.

Related Art

As a method of evaluating pore distribution in a material or a specific surface area of the material, a gas adsorption method is used. For example, an adsorption characteristic measuring apparatus, which measures an adsorption isotherm using a constant volume method to evaluate a specific surface area or a pore distribution, includes a plurality of pressure gauges, valves, and a vacuum exhaust system to supply a predetermined number of moles of adsorbate to a sample in the sample tube, which is set to constant volume and temperature, and to measure the pressure change before and after adsorption.

JP 2014-81250A discloses an example where a powder sample is accommodated in a sample tube made of glass, a nitrogen gas is used as an adsorbate, the sample tube is disposed in a Dewar vessel filled with liquid nitrogen, and a pressure change in the sample tube is measured under a constant liquid nitrogen temperature of 77 K.

As a technique related to the invention, JP 2008-247702A discloses a method of producing a zeolite film, which is formed on a surface of a porous tubular support body made of ceramic such as alumina, as a separation film by which carbon monoxide is selectively separated from a hydrocarbon gas.

A zeolite film formed body disclosed in JP 2008-247702A is configured such that a thin zeolite film is formed on the surface of the support body and is used in a composite structure where the support body and the zeolite film are integrated. The sample object used for the measurement of adsorption characteristics is generally in the form of a powder or the like. However, since the zeolite film formed body has the integrated composite structure, it is meaningless to try to measure the adsorption characteristics even though using powder of the zeolite film and the support body in a mixed state. Each of the zeolite film and the support body can be separately powdered to measure adsorption characteristics, but it is not possible to evaluate the adsorption characteristics of the zeolite film formed body. Therefore, in the case of trying to measure the adsorption characteristics in an intact form of the zeolite film formed body, the size of the sample tube becomes larger, a dead volume increases, and measurement accuracy of the adsorption characteristics is lowered.

Furthermore, in the zeolite film formed body, zeolite crystals having micropores are aggregated in an amorphous form and an inter-crystal void has a size of mesopores or macropores. Here, the micropore refers to a pore having a diameter of less than 2 nm, the mesopore refers to a pore having a diameter from 2 nm to 50 nm, and the macropore refers to a pore having a diameter of larger than 50 nm. As the diameter of the pores becomes smaller, an adsorption layer of an adsorption gas becomes thinner and discrete adsorption proceeds. In addition, since heat of adsorption is generated at the time of the adsorption, there is a problem that adsorption equilibrium is difficult to attain. In order to measure the adsorption amount of gas molecules which are discretely and thinly adsorbed using a constant volume method, it is necessary to measure an adsorption isotherm with high accuracy under very low relative pressure. The adsorption gas is lean under the very low relative pressure and has a thermal conductivity lower than that of an adsorption gas having higher pressure, and thus it is difficult to maintain the sample, which passes through the sample tube from a refrigerant tank used to maintain an isothermal state, at a predetermined constant temperature. Herein, the relative pressure is a pressure of the adsorption gas normalized by a saturated vapor pressure of the adsorption gas and has a dimensionless value.

In order to obtain the adsorption isotherm of the film formed body with high accuracy as described above, there are problems in that the measurement should be performed with high accuracy under the very low relative pressure, so that the influence of the heat distribution in the sample tube is eliminated. Until now, measuring the adsorption isotherm of the film formed body itself with high accuracy has not been performed.

SUMMARY

An object of the invention is to provide an adsorption characteristic measuring apparatus capable of obtaining an adsorption isotherm for a film formed body or a formed body with high accuracy.

According to the invention, there is provided an adsorption characteristic measuring apparatus that supplies a predetermined adsorption gas to a sample accommodated in a sample tube to measure an adsorption isotherm, the apparatus including: a refrigerant container that is filled with a constant temperature refrigerant having the sample tube immersed therein; a fitting portion that is provided at an opening of the sample tube; an adsorption gas supply portion that supplies the adsorption gas; a manifold that is connected via an on-off valve for the sample tube to the fitting portion; a manifold pressure gauge that detects a pressure of the manifold; a sample tube pressure gauge that detects an internal pressure of the sample tube; and a measurement controller that calculates the adsorption isotherm based on a change in the internal pressure of the sample tube, wherein the sample is a film formed body or a formed body, and a space between an inner wall surface of the sample tube and the sample is filled with a particle-like filler having higher thermal conductivity than the adsorption gas under a measurement pressure.

Furthermore, in the adsorption characteristic measuring apparatus according to the invention, the particle-like filler may be metal particles.

Furthermore, in the adsorption characteristic measuring apparatus according to the invention, the particle-like filler may be aluminum particles.

Furthermore, in the adsorption characteristic measuring apparatus according to the invention, the inside of the sample tube may be disposed with: a dead volume reducing rod that is made of the same material as the sample tube to reduce an upper dead volume of a sample-side region which is a region around the sample filled with the particle-like filler; and a spacer ring that is provided between a bottom side of the dead volume reducing rod and an upper surface side of the sample-side region and has lower thermal conductivity than the particle-like filler.

Furthermore, in the adsorption characteristic measuring apparatus according to the invention, the apparatus may further include a reflection plate that adheres to the bottom side of the dead volume reducing rod to reflect radiant heat from the sample-side region and the dead volume reducing rod.

Furthermore, in the adsorption characteristic measuring apparatus according to the invention, the fitting portion may be a joint that is used such that metal surfaces are airtightly held by being abutted against each other.

Furthermore, in the adsorption characteristic measuring apparatus according to the invention, the film formed body may be formed with a film having pores having different diameters from micropores to macropores, on a surface of a tubular support body, and the formed body may have pores having different diameters from micropores to macropores.

According to the adsorption characteristic measuring apparatus having the above configuration, the space between the sample of the film formed body or the formed body and the inner wall surface of the sample tube is filled with the particle-like filler having the higher thermal conductivity than the adsorption gas under the measurement pressure. Thus, the thermal conductivity between the sample tube and the sample is improved, and thus the adsorption isotherm can be obtained with high accuracy even when the pressure of the adsorption gas is below a very low relative pressure.

In addition, since the particle-like filler may be the metal particle, it has predominantly higher thermal conductivity than the gas. Since the metal particles are filled in the space between the sample of the film formed body and the inner wall surface of the sample tube, the thermal conductivity between the sample tube and the sample is significantly improved. In addition, since the particle-like filler may be aluminum particles, it is inexpensively and easily available.

Furthermore, in the adsorption characteristic measuring apparatus, the inside of the sample tube may be provided with the dead volume reducing rod that is disposed at the upper side of the sample tube in which the sample is placed and the spacer ring that is disposed between the bottom side of the dead volume reducing rod and the upper surface side of the sample-side region and has the lower thermal conductivity than the particle-like filler. By the arrangement of the spacer ring, the thermal insulation space is formed between the dead volume reducing rod and the sample-side region. Thus, it is possible to effectively eliminate the influence of the heat inside the dead volume and to obtain the adsorption isotherm with excellent accuracy.

Moreover, since the reflection plate adheres to the bottom side of the dead volume reducing rod to reflect the radiant heat from the sample-side region and the dead volume reducing rod, it is possible to further effectively eliminate the influence of the heat inside the dead volume and to achieve the adsorption isotherm with high accuracy.

Furthermore, in the adsorption characteristic measuring apparatus, the fitting portion used for the connection of the sample tube and a pipe portion may be a joint that is used such that the metal surfaces are airtightly held by being abutted against each other. Thus, the gas is not released from the material of the joint and the adsorption isotherm can be obtained with higher accuracy.

In addition, even when the measurement object is the film formed body that was formed with a film having pores having different diameters from micropores to macropores, on the surface of the tubular support body, or the formed body that has pores having different diameters from micropores to macropores, it is possible to obtain the adsorption isotherm with high accuracy in a wide range from the measurement of the micropores under the very low temperature and the very low relative pressure to the measurement of the macropores at a high relative pressure

DETAILED DESCRIPTION OF PREFERRED EMBODIMENTS

A detailed description will hereinafter be given of an embodiment of the present invention with reference to the drawings. In the following description, as a measurement sample, a film formed body is employed in which a zeolite film is formed on a surface of a ceramic support body, but this is merely an example for description. Thus, the measurement sample may be a formed body having micropores, mesopores, and macropores.

In addition, a nitrogen gas is employed as an adsorption gas in the following description, but is merely an example. Thus, other gases may be employed. Furthermore, it is assumed that a dead volume is calculated using a helium gas which is adsorbed onto a sample even at a nitrogen adsorption temperature. However, an internal volume of a sample tube and a volume defined by an outer shape of the sample are measured in advance and a difference between the internal volume and the volume may be used as a dead volume. The volume of the sample may be obtained from a true density of the sample and a mass of the sample.

Shapes, dimensions, materials and the like to be described below are exemplified and can be appropriately changed according to specifications of the adsorption characteristic measuring apparatus. In the following description, corresponding components are denoted by the same reference numerals in all of the drawings and duplicated description thereof will not be given.

Figure 1:
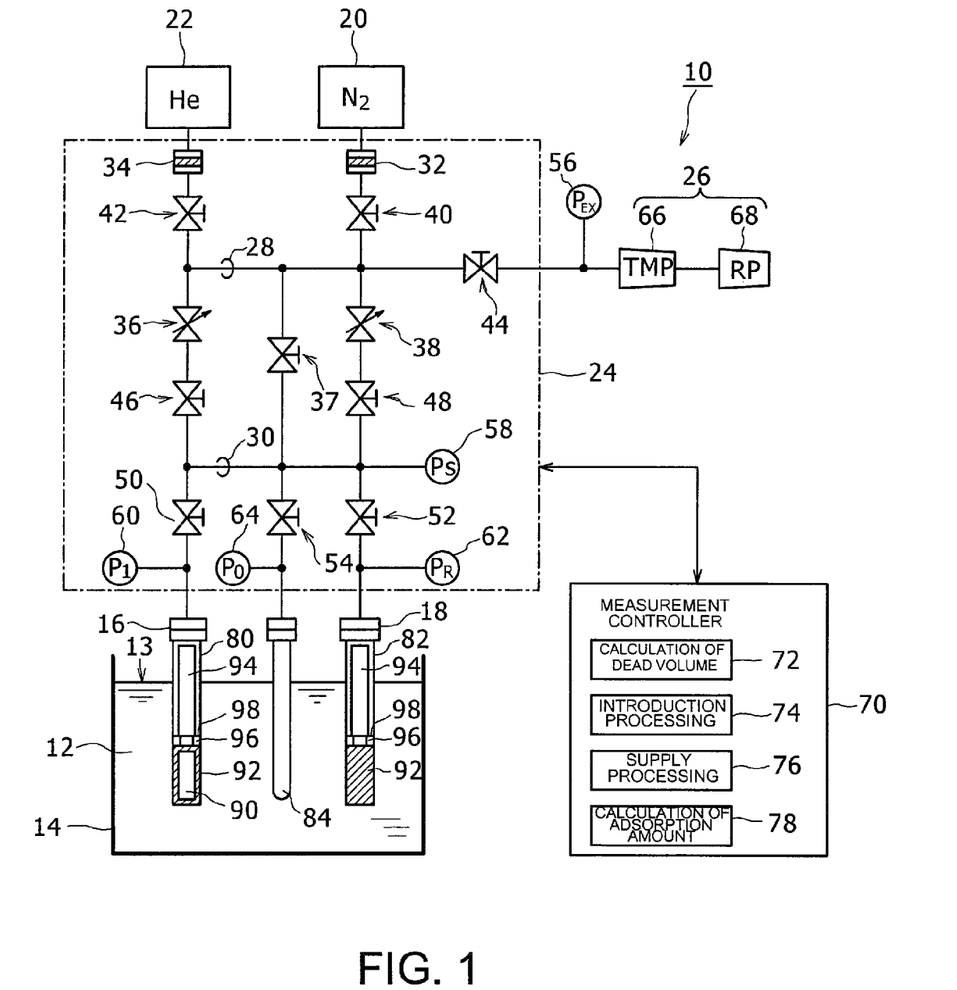
FIG. 1 is a diagram illustrating a configuration of an adsorption characteristic measuring apparatus according to an embodiment of the invention.

FIG. 1 is a block diagram of an adsorption characteristic measuring apparatus 10. In FIG. 1, although not components of the adsorption characteristic measuring apparatus 10, two sample tubes 80 and 82 are illustrated. The sample tube 80 is a measurement sample tube in which a film formed body 90 is accommodated as a sample. The sample tube 82 is a reference sample tube that is used to correct the influence according to gradual lowering of the liquid level 13 of the refrigerant 12 during the measurement period. The film formed body 90 as the sample is not disposed in the sample tube 82.

The adsorption characteristic measuring apparatus 10 illustrated in FIG. 1 has the same configuration as a general adsorption characteristic measuring apparatus, which measures an adsorption amount of an adsorption gas adsorbed onto a sample based on an adsorption isotherm using a constant volume method, except for the sample tubes 80 and 82 and members disposed inside the sample tubes 80 and 82. Therefore, first, the description will be given on the sample tubes 80 and 82 and each of the members disposed inside the sample tubes 80 and 82 which are features in terms of use of the adsorption characteristic measuring apparatus 10, and then configuration and operation of the adsorption characteristic measuring apparatus 10 fitted with the sample tubes 80 and 82 will be described.

As illustrated in FIG. 1, the inside of the sample tube 80 as the measurement sample tube is disposed with a particle-like filler 92, a glass rod 94, a spacer ring 96, and a reflection plate 98 in addition to the film formed body 90. The inside of the sample tube 82 as the reference sample tube is disposed with the same members as those disposed inside the sample tube 80 except that the film formed body 90 as the sample is not disposed. In the sample tube 82, the particle-like filler 92 is filled in a space corresponding to the film formed body 90 of the sample tube 80.

Figure 2A:
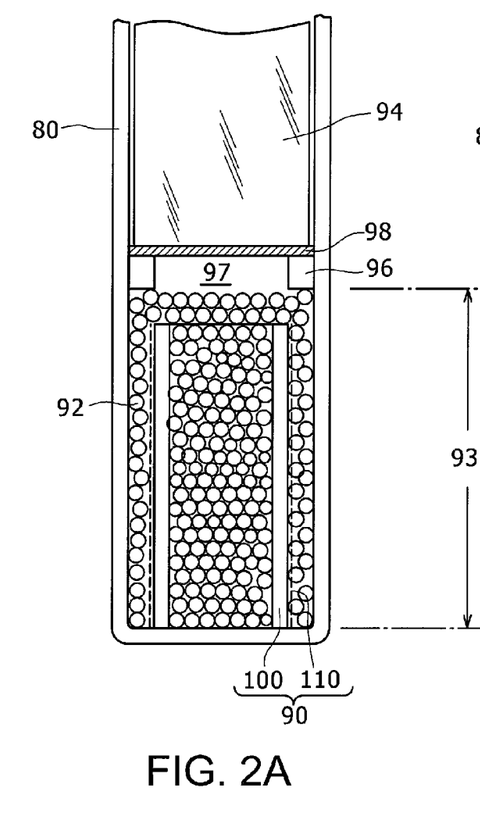
FIG. 2A is a detailed view of one of two sample tubes illustrated in FIG. 1.
Figure 2B:
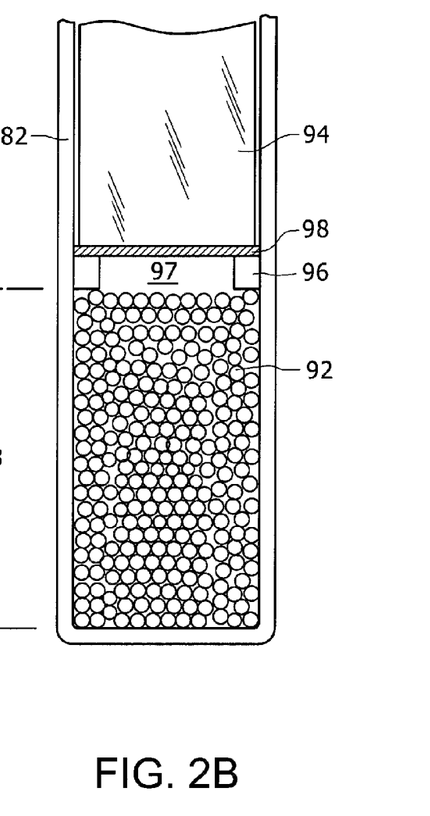
FIG. 2B is a detailed view of the other of two sample tubes illustrated in FIG. 1.

FIGS. 2A and 2B are diagrams illustrating insides of the tubes using cross-sectional views of the sample tubes 80 and 82, respectively. FIG. 2A is a cross-sectional view of the sample tube 80, and FIG. 2B is a cross-sectional view of the sample tube 82.

Each of the sample tubes 80 and 82 is a sample container in which one end is an elongated tube having an end opening and an inner space of the other end as a bottom is an accommodation portion capable of accommodating the sample. As such sample tubes 80 and 82, glass sample tubes having uniform outer and inner diameters can be used. By way of example, each of the sample tubes 80 and 82 has a dimension where the inner diameter is about 12 mm, the outer diameter is about 14 mm, and a length is about 200 mm. Depending on the purpose of measurement, a sample tube made of Pyrex (registered trademark), quartz and the like may be used.

The film formed body 90 as the sample is a zeolite film formed body. The zeolite film formed body, in which a thin zeolite film 110 is formed on a peripheral surface of a support body 100, has a composite structure where the support body 100 and the zeolite film 110 are integrated. Although not illustrated in FIG. 2A, the zeolite film is also formed on circular tube-like upper surface and lower surface of the support body 100. In some cases, the zeolite film may also be formed on a circular tube-like inner peripheral surface of the support body 100 and the zeolite film may be formed only on the circular tube-like inner peripheral surface of the support body 100.

The support body 100 is a tube member made of α-alumina. By way of example, the support body 100 has a dimension where the inner diameter is about 7 mm, the outer diameter is about 10 mm, and a length is about 40 mm. The zeolite film 110 was obtained in such a manner that a seed crystal was held on the support body 100 by a dip coating method and the seed crystal was subjected to crystallization for 12 hours while being kept at a temperature of 453 K in an aqueous gel of (36 SiO2:15 Al2O3:8 Na2O:1200 H2O). By way of example, the thickness of the zeolite film 110 is about 0.5 mm.

Figure 3:
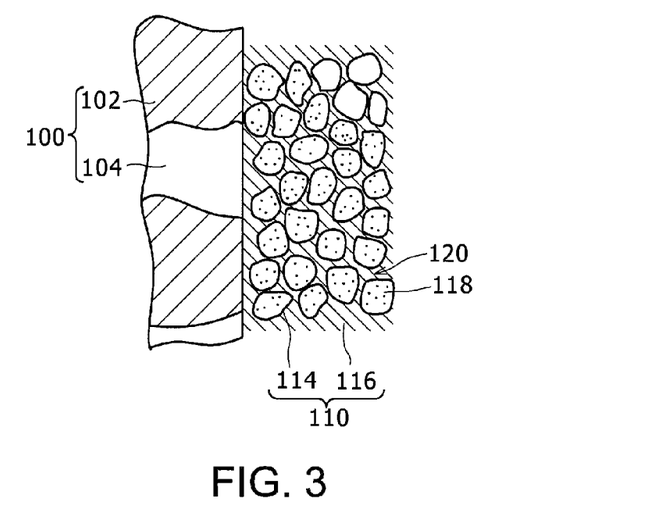
FIG. 3 is a detailed view of a film formed body illustrated in FIG. 2A.

FIG. 3 is a cross-sectional view of an outer peripheral side of the film formed body 90. The support body 100 is an a-alumina porous body and includes a base body 102 and a pore 104. The pore 104 is a macropore having an average diameter of about 150 nm. The zeolite film 110 is a film made of a composition called as Na-ZSM-5. The zeolite film 110 is configured to include a plurality of zeolite crystals 114 of ZSM-5 and an amorphous layer 116 on which the plurality of zeolite crystals 114 are aggregated. The zeolite crystal 114 includes pores 118 having a small diameter. Regarding to the diameter of the pore 118, the pore 118 is a micropore having a diameter of less than 2 nm. The size of the zeolite crystal 114 is about 1 μm in diameter. The amorphous layer 116 between the zeolite crystals 114 is an inter-crystal void 120 with a thickness of several nm to 100 nm. The inter-crystal void 120 having such a size is a pore corresponding to a mesopore or a macropore. Thus, the zeolite film 110 is a pore film including pores having a wide range of diameters, for example, micropores, mesopores, and macropores which are mixed.

Returning again to FIG. 2A, members accommodated inside the sample tube 80 will be described with reference to FIG. 2A. The film formed body 90 having the outer diameter of about 10 mm is inserted into the sample tube 80 having the inner diameter of about 12 mm. Since the film formed body 90 as the sample has a cylindrical outer shape, it differs from a powder-like sample and does not come in close contact with an inner wall surface of the sample tube 80, and thus a void is formed between the film formed body 90 and the inner wall surface of the sample tube 80. The adsorption gas is filled in the void, but becomes a lean gas similar to a vacuum under a very low relative pressure, and has a low thermal conductivity.

The particle-like filler 92 is a member which is filled in the void formed between the inner wall surface of the sample tube 80 and the film formed body 90 to improve the thermal conductivity between the sample tube 80 and the film formed body 90. The particle-like filler 92 is a substance onto which the adsorption gas is not adsorbed, and a substance having a thermal conductivity higher than that of the adsorption gas under a measurement pressure is used as the particle-like filler 92. The particles have a size of an outer diameter smaller than a dimension difference between the inner diameter of the sample tube 80 and the outer diameter of the film formed body 90. When the outer diameter of the particles becomes considerably smaller and thus the particles are turned into a powder shape, a specific surface area increases and the adsorption gas may be adsorbed. Therefore, an appropriate particle size may be selected so as not to absorb gas. As such a particle-like filler 92, metal particles having an outer diameter of about 1 mm can be used. Herein, aluminum particles having an outer diameter of about 1 mm are used.

The particle-like filler 92 is filled in the void formed between the inner wall surface of the sample tube 80 and the outer peripheral surface of the film formed body 90, in a hollow on an inner peripheral side of the film formed body 90, and on the upper surface side of the film formed body 90. If necessary, the particle-like filler 92 may be filled between the lower surface side of the film formed body 90 and the inner bottom of the sample tube 80. In FIG. 2A, the particle-like filler 92 is filled up to a height position indicated by a sample-side region 93 from the bottom of the sample tube 80. The height of the sample-side region 93 may satisfy the relation of {(length of film formed body 90)+ (thickness corresponding to two or three layers of particle-like filler 92)}.

The glass rod 94 is a dead volume reducing rod which is inserted into the sample tube 80 to reduce an internal dead volume of the sample tube 80. The dead volume is an apparent volume obtained by converting a space among an inner space of the sample tube 80, to which the adsorption gas is supplied and is cooled to a constant temperature to obtain the adsorption isotherm, into a space under an apparatus temperature (room temperature), and corresponds to a volume difference between an inner volume of the sample tube 80 and an external volume of the sample 90.

The glass rod 94 is formed of the same material as that of the sample tube 80. When the sample tube 80 is formed of Pyrex (registered trademark) or quartz, the glass rod 94 is preferably a Pyrex glass rod or a quartz glass rod. The glass rod 94 may be a suitable colored glass. The outer diameter of the glass rod 94 is set to be slightly smaller than the inner diameter of the sample tube 80. A position of the bottom of the glass rod 94 inside the sample tube 80 is set to a height position separated by an appropriate thermal insulation space 97 from the upper surface of the sample-side region 93 in which the film formed body 90 and the particle-like filler 92 are disposed. As illustrated in FIG. 1, an upper end position of the glass rod 94 is set to a position which is sufficiently higher than the liquid level position of the refrigerant 12 in a refrigerant container 14 in a height direction of the sample tube 80, and sufficiently lower than the height position of the end opening of the sample tube 80. In the example where the length of the sample tube 80 is 200 mm and the length of the film formed body 90 is 40 mm, when the height of the sample-side region 93 is set to be 44 mm and the height of the thermal insulation space 97 is set to be 3 mm, the length of the glass rod 94 is set to be about 140 to 145 mm, which is shorter than 153 mm ((200−44−3) mm).

The spacer ring 96 is an annular member which is placed on the upper surface of the particle-like filler 92 in the sample-side region 93 so as to form the thermal insulation space 97 for thermally insulating the sample-side region 93 and the glass rod 94 from each other. The height of the thermal insulation space 97 can be determined in terms of thermal insulation of a temperature difference between a temperature of the sample-side region 93, that is, 77 K under the measurement of the adsorption isotherm and a temperature of the upper end side of the glass rod 94, that is, room temperature. When the adsorption gas is a nitrogen gas, the height of the thermal insulation space 97 is preferably several mm. The height of the thermal insulation space 97 is determined by the height of the spacer ring 96. If it is necessary to set the height of the thermal insulation space 97 to be 3 mm, the height of the spacer ring 96 is set to be 3 mm.

Such a spacer ring 96 may be a ring made of a material having a lower thermal conductivity than the particle-like filler 92. For example, the ring can be made of glass that is similar to the sample tube 80 and the glass rod 94. The inner diameter of the spacer ring 96 can be made as wide as possible to ensure the thermal insulation space 97. By way of example, the inner diameter of the sample tube 80 can be set to be 12 mm, the outer diameter of the spacer ring 96 can be set to be 11.5 mm, and the inner diameter of the spacer ring 96 can be set to be about 10 to 10.5 mm.

The reflection plate 98 is a double-sided reflective film which reflects radiant heat from the sample-side region 93 side and the glass rod 94 side. The reflection plate 98 is disposed on the bottom side of the glass rod 94. As the reflection plate 98, a metal foil can be used. Herein, as the reflection plate 98, an aluminum foil is used, and the aluminum foil is attached to the bottom of the glass rod 94. In order to reduce heat flow between the reflection plate 98 and the glass rod 94, the reflection plate 98 preferably adheres to a portion of the bottom of the glass rod 94 to the extent of being held without being detached from the glass rod 94, rather than adhering to the entire surface thereof. Ideally, the reflection plate 98 is preferably attached at a single point to the glass road 94.

FIG. 2B is a cross-sectional view of the sample tube 82 as a reference sample tube. The film formed body 90 as the sample is not provided inside the sample tube 82, and the particle-like filler 92 is uniformly filled up to the height of the sample-side region 93 in the inner space of the sample tube 82. The glass rod 94, the spacer ring 96, and the reflection plate 98 are disposed in the same manner as described for the sample tube 80.

The description of the sample tubes 80 and 82 and each of the members disposed inside the sample tubes 80 and 82 is concluded as described above, and returning again to FIG. 1, the configuration and operation of the adsorption characteristic measuring apparatus 10 attached with the sample tubes 80 and 82 will be described.

The adsorption characteristic measuring apparatus 10 is configured to include: the sample tubes 80 and 82; the refrigerant container 14 that is filled with the constant-temperature refrigerant 12 into which a saturated vapor pressure pipe 84 is immersed; fitting portions 16 and 18 that are provided at the openings of the sample tubes 80 and 82, respectively; an adsorption gas source 20 from which a nitrogen gas as an adsorption gas is supplied; a helium gas source 22 from which a helium gas is supplied to determine the dead volume; a pipe portion 24 including a plurality of on-off valves and pressure gauges; an exhaust pump 26; and a measurement controller 70.

The refrigerant container 14 is a Dewar vessel which is disposed with the sample tubes 80 and 82 and the saturated vapor pressure pipe 84 at the inner space, and the refrigerant 12 is filled around the sample tubes 80 and 82 and the saturated vapor pressure pipe 84 to maintain the sample tubes 80 and 82 and the saturated vapor pressure pipe 84 at a predetermined constant temperature. In FIG. 1, the liquid level 13 of the refrigerant 12 related to the dead volume of the sample tubes 80 and 82 is illustrated. The type of the refrigerant 12 is selected according to the type of the adsorption gas. However, when the adsorption gas is a nitrogen gas, the refrigerant 12 may be liquid nitrogen. In this case, the predetermined constant temperature is 77 K. The saturated vapor pressure pipe 84 is a pipe that is filled with the adsorption gas and is provided to always detect the saturated vapor pressure of the adsorption gas at the predetermined constant temperature during the measurement period. When the adsorption gas is the nitrogen gas, the saturated vapor pressure pipe 84 always detects the saturated vapor pressure $P_0$ at the temperature of 77 K.

The fitting portions 16 and 18 are connection joints that are used to connect the end openings of the sample tubes 80 and 82 with sample-tube connection ports of the pipe portion 24, respectively. In the related art, the sample tubes are connected to the pipe portion using, for example, an electromagnetic valve, an air actuated valve, and a coupling joint, but since a rubber material or a plastic material is used for a sealing material, a gas released by such a sealing material had an influence on the measurement. For example, due to the released gas, the inside of the sample tubes could not be sufficiently exhausted by the exhaust pump, the degree of ultimate vacuum did not sufficiently reach a low pressure, or accuracy of the adsorption isotherm under a very low relative pressure was reduced by the influence of the released gas during the adsorption measurement.

Therefore, as the fitting portions 16 and 18, a rubber material or a plastic material is not used, but joints are used such that metal surfaces are airtightly held by being abutted against each other. As these fitting portions 16 and 18, VCR (registered trademark) made by Cajon Company can be used.

The adsorption gas source 20 indicated as N2 in FIG. 1 is an adsorption gas supply portion that supplies the adsorption gas as an object for measuring adsorption characteristics to the film formed body 90, which is the sample. Herein, since the adsorption gas is a nitrogen gas, the adsorption gas source 20 a nitrogen gas cylinder.

The helium gas source 22 indicated as He in FIG. 1 is a gas cylinder filled with helium gas used to measure the dead volume of the sample tubes 80 and 82. In the measurement of the dead volume when the adsorption gas is the nitrogen gas, it is necessary to use an inert gas which is not adsorbed onto the sample tubes 80 and 82 even at a nitrogen adsorption temperature, and helium gas is suitable for such a purpose.

The pipe portion 24 is configured by a plurality of pipes that are used to connect the sample tubes 80 and 82, the adsorption gas source 20, the helium gas source 22, and the exhaust pump 26 with each other through manifolds 28 and 30 provided therebetween. The pipe portion 24 includes: two flow-rate regulating valves 36 and 38 that are configured to manually set flow rates together with filters 32 and 34; on-off valves 37 and 40 to 54 that are operated under the control of the measurement controller 70; and pressure gauges 58 to 64. The pressure gauge 56 is disposed outside of the pipe portion 24. In two flow-rate regulating valves 36 and 38 and the on-off valves 40 to 54, an air actuated valve is used instead of an electromagnetic valve. This makes it possible to reduce the released gas from two flow-rate regulating valves 36 and 38 and the on-off valves 40 to 54 and to perform the adsorption characteristic measurement with high accuracy. In order to ensure the adsorption characteristic measurement with high accuracy, the entire pipe portion 24 is accommodated in a temperature-adjusted bath and is maintained at a predetermined reference temperature $T_S$.

In the pipe portion 24, the filter 32 and the on-off valve 40 are connected to each other in series between the adsorption gas source 20 and the manifold 28. Similarly, the filter 34 and the on-off valve 42 are connected to each other in series between the helium gas source 22 and the manifold 28. The filters 32 and 34 are filtration units for removing foreign substances and the like contained in the helium gas and the nitrogen.

The manifold 28 is a pipe line that is used as a gas supply buffer when the nitrogen gas and the helium gas are supplied toward the sample tubes 80 and 82 from the adsorption gas source 20 and the helium gas source 22, respectively, and is used as an exhaust buffer when the insides of the sample tubes 80 and 82 are exhausted.

The manifold 28 is connected to the exhaust pump 26 through the on-off valve 44. The pressure gauge 56 is an exhaust pressure detecting portion for detecting a pressure PEX of a gas to be exhausted from the manifold 28 when the on-off valve 44 is turned on.

Two flow-rate regulating valves 36 and 38 and two on-off valves 46 and 48 provided between the manifold 28 and the manifold 30 have a function of circulating the gas while adjusting the flow rate between the manifold 28 and the manifold 30. Herein, a pipe line through which the flow-rate regulating valve 36 and the on-off valve 46 are connected to each other in series, and a pipe line through which the flow-rate regulating valve 38 and the on-off valve 48 are connected to each other in series, are disposed in parallel with each other. The flow-rate regulating valve 36 is a rough flow-rate regulating valve that roughly adjusts the flow rate of the gas flowing between the manifold 28 and the manifold 30, and the flow-rate regulating valve 38 is a fine flow-rate regulating valve that finely adjusts the flow rate of the gas flowing between the manifold 28 and the manifold 30. The on-off valves 46 and 48 are valves that are switched to open or close stat. It is possible to appropriately adjust the flow rate of the gas between the manifold 28 and the manifold 30 by setting the degree of opening of two flow-rate regulating valves 36 and 38 and controlling the on-off states of the two on-off valves 46 and 48. For example, when the on-off valve 46 is turned on for a predetermined time while the on-off valve 48 is turned off, the flow rate can be roughly adjusted, and then when the on-off valve 48 is turned on for a predetermined time while the on-off valve 46 is turned off, the fine flow-rate adjustment can be additionally performed.

The on-off valve 37 provided between the manifold 28 and the manifold 30 is a bypass valve. For example, the on-off valve 37 is turned on when the manifold 28 and the manifold 30 need to be evacuated to a predetermined degree of vacuum during the setting of an initial state.

The manifold 30 is used as a space into which the helium gas from the helium gas source 22 is temporarily introduced when being supplied to either of the sample tubes 80 and 82 to measure the dead volume. In addition, the manifold 30 is used as a space into which the nitrogen gas from the adsorption gas source 20 is temporarily introduced when being supplied to either of the sample tubes 80 and 82 to measure adsorption characteristics. The on-off valve 54 is turned on when the nitrogen gas is supplied to the manifold 30 and thus the nitrogen gas is supplied to the saturated vapor pressure pipe 84. In this way, the volume of the pipe line of manifold 30 is a reference volume $V_S$ at the time of the supply of the helium gas for the measurement of the dead volume, and a reference volume $V_S$ at the time of the supply of the nitrogen gas for the measurement of the adsorption characteristics. A temperature of the manifold 30 is a reference temperature $T_S$ at which the pipe portion 24 is maintained by the temperature-adjusted bath.

The pressure gauge 58 is a manifold pressure detecting portion for detecting an internal pressure $P_S$ of the manifold 30. The internal pressure $P_S$ is an initial pressure of the nitrogen gas to be supplied to the sample tube 80 during the measurement of the adsorption characteristics in the reference volume $V_S$.

In the pipe portion 24, the on-off valves 50 and 52 are connected to the pipes provided between the sample tubes 80 and 82 and the manifold 30, respectively, and the on-off valve 54 is connected to the pipe provided between the saturated vapor pressure pipe 84 and the manifold 30. To describe the sample tube 80, a pipe for the sample tube 60, one end of which is connected to the fitting portion 16 attached to the end opening of the sample tube 80 and the other end of which is connected to a connection port provided in the manifold 30, is provided in series with the on-off valve 50 between the one end and the other end of the pipe. The pressure gauge 60 is a sample-tube pressure detecting portion that is connected to the pipe between the fitting portion 16 and the on-off valve 50 to detect an internal pressure P1 of the sample tube 80.

Similarly, a pipe for the sample tube 82 is configured in such a manner that the on-off valve 52 is connected to the fitting portion 18 that is attached in series to the end opening of the sample tube 82 and the manifold 30. The pressure gauge 62 is a reference-sample-tube pressure detecting portion that is connected to the pipe between the fitting portion 18 and the on-off valve 52 to detect an internal pressure PR of the sample tube 82, which is a reference sample tube. Since the detection value of the pressure gauge 62 is related to a magnitude of the liquid level 13 of the liquid nitrogen as the refrigerant 12 which gradually lowers during the measurement period, the calculation of the dead volume is corrected based on the detection value.

The VCR (registered trademark) similar to the fitting portions 16 and 18 or Swagelok (registered trademark) made by Crawford Fitting Co. is attached to the end opening of the saturated vapor pressure pipe 84, as a joint. The on-off valve 54 is connected to the joint and the manifold 30 in series, thereby forming a pipe for the saturated vapor pressure pipe 84. The pressure gauge 64 is a saturated vapor pressure detecting portion that detects the saturated vapor pressure $P_0$ of the nitrogen gas as the adsorption gas supplied to the saturated vapor pressure pipe 84 at the temperature of 77 K.

The exhaust pump 26 is an exhaust apparatus for reducing an internal pressure of the sample tubes 80 and 82 through the manifolds 30 and 28. The exhaust pump 26 can be used in combination with a turbo molecular pump 66 indicated as a TMP in FIG. 1 and a rotary pump 68 indicated as an RP. The rotary pump 68 continues to be actuated during use of the adsorption characteristic measuring apparatus 10, but the turbo molecular pump 66 appropriately is actuated and stopped under the control of the measurement controller 70.

The measurement controller 70 is a controller having functions of controlling on and off states of the on-off valves 37 and 40 to 54 in the pipe portion 24 and measuring the adsorption characteristics using the detection values of the pressure gauges 58 to 64. Such a measurement controller 70 can be configured in a suitable computer.

The measurement controller 70 has functions of executing: a dead volume calculating step 72; an introduction processing step 74 of introducing the adsorption gas of the reference volume into the manifold 30; a supply processing step 76 of supplying the introduced adsorption gas of the reference volume to the sample tubes 80 and 82; and an adsorption amount calculating step 78 of calculating the adsorption amount on the film formed body 90 in the sample tube 80.

In the dead volume calculating step 72, the dead volume can be calculated based on the internal volume of the sample tubes 80 and 82 and the volume of the sample. In the case of a method of calculating the dead volume by introducing the helium gas into the sample tubes 80 and 82, however, once the helium gas has been introduced into the sample tubes 80 and 82, it is difficult to completely remove the helium gas even when the gas inside of the sample tubes 80 and 82 is exhausted by the exhaust pump 26, for example. If the inside of the sample tubes 80 and 82 remains contaminated by the residual helium gas, it is difficult to obtain the adsorption isotherm with high accuracy. For this reason, the dead volume calculating step 72 shall be performed after the introduction processing step 74 and the supply processing step 76.

Such functions can be implemented by execution of software in the measurement controller 70. Specifically, the functions can be implemented by execution of an adsorption characteristic measuring program. Some of these functions may be implemented by hardware.

In the above configuration, the adsorption characteristics are measured by the following steps. When the adsorption characteristic measuring program starts to execute, the adsorption characteristic measuring apparatus 10 is initialized. In FIG. 1, the initial state is a state where the end opening of the sample tube 80 accommodating the film formed body 90 as the sample therein is connected to the fitting portion 16 and all of the on-off valves 37 and 40 to 54 are turned off in a state where the degree of opening of the flow-rate regulating valves 36 and 38 are manually set in advance. A temperature of the pipe portion 24 including the manifold 30 is a predetermined temperature $T_S$.

Subsequently, the manifolds 28 and 30 are pulled by the exhaust pump 26 until a predetermined degree of vacuum so as to measure the adsorption isotherm with high accuracy. Here, the exhaust pump 26 is actuated and thus the on-off valve 44 and the on-off valve 37 as a bypass valve are turned on. When it is confirmed using the pressure gauges 56 and 58 that the manifolds 28 and 30 are in the state of the predetermined degree of vacuum, the process proceeds to the next step.

When the manifolds 28 and 30 are in the state of the predetermined degree of vacuum, the on-off valve 50 is turned on and the sample tube 80 is continuously pulled by the exhaust pump 26 until a predetermined degree of vacuum. When it is confirmed using the pressure gauges 56, 58, and 60 that the sample tube 80 is in the state of the predetermined degree of vacuum, the on-off valve 50 is turned off, the pressure gauge 60 is monitored, and the released gas is checked as to whether the internal pressure of the sample tube 80 increases. After a predetermined prescribed time, when a change in the detection value of the pressure gauge 60 is in a predetermined allowable range, the process further proceeds to the next step. If there is a problem, investigation of the cause is performed.

When the change in the internal pressure of the sample tube 80 is in the allowable range, all of the on-off valves 37 and 40 to 54 return to the off state. Thus, the refrigerant 12 is filled in the refrigerant container 14 and the sample tubes 80 and 82 and the saturated vapor pressure pipe 84 are immersed in the refrigerant 12. As a result, the sample tubes 80 and 82 and the saturated vapor pressure pipe 84 become a temperature of 77 K.

In this way, when the initial state is completed, the on-off valve 50 is set to be in the on state, the on-off valves 46 and 48 are sequentially set to be in the on state, and the on-off valve 44 is set to be in the on state, whereby the exhaust pump 26 is actuated. Thus, the internal pressure of the sample tube 80 and the internal pressure of the manifolds 30 and 28 are sufficiently reduced to be in a state similar to a vacuum. Subsequently, all of the on-off valves 37 and 40 to 54 return to the off state, and the actuation of the turbo molecular pump 66 in the exhaust pump 26 stops.

Next, the processing of introducing the nitrogen gas as the adsorption gas into the manifold 30 is performed. This processing is executed by the function of the introduction processing step 74 in the measurement controller 70. The step of introducing the nitrogen gas into the manifold 30 is performed as follows. That is, the on-off valve 40 is set to be in an on state, and the on-off valves 46 and 48 are sequentially set to be in an off state. Thus, the nitrogen gas is introduced into the manifold 30 from the adsorption gas source 20. All of the on-off valves 37 and 40 to 54 return to the off state at an appropriate time, and at this time, a pressure of the manifold 30 is detected by the pressure gauge 58. When the detected pressure is defined as $P_S$, a temperature and a pressure of the nitrogen gas introduced into the manifold 30 are defined as a reference temperature $T_S$ and a pressure $P_S$, respectively, and a volume thereof is defined as a reference volume $V_S$.

Subsequently, the processing of supplying the nitrogen gas of the manifold 30 to the sample tube 80 is performed. This processing is executed by the function of the supply processing step 76 in the measurement controller 70. The off state of the on-off valve 50 is switched to the on state so as to supply the nitrogen gas to the sample tube 80 from the manifold 30. Then, the pressure of the sample tube 80 and the manifold 30 is detected by the pressure gauge 58 or the pressure gauge 60. The detected pressure is defined as $P_1$.

In the above, it is assumed that one introduction processing step and one supply processing step are performed. From the viewpoint of high accuracy in the calculation value of the adsorption amount, shortening of the measurement time and the like, however, the introduction processing step and the supply processing step may be repeatedly performed as a set of processing steps. For example, a first set of introduction processing and supply processing steps is performed to obtain the pressure of the sample tube 80 in the equilibrium state as $P_1$ (1) and the pressure of the manifold 30 as $P_S$ (1), a second set of introduction processing and supply processing steps is subsequently performed to obtain the pressure of the sample tube 80 in the equilibrium state as $P_1$ (2) and the pressure of the manifold 30 as $P_S$ (2), and these steps are repeated. When the calculation of the adsorption amount to be described below is performed based on the obtained several sets of $P_1$ (n) and $P_S$ (n), the calculation value of the adsorption amount can be achieved with high accuracy.

Finally, the dead volumes of the sample tubes 80 and 82 are calculated. This processing step is executed by the function of the dead volume calculating step 72 in the measurement controller 70. Since the calculation processing of a dead volume $V_D$ is performed on both of the sample tubes 80 and 82 in the same manner, the description will now be made with respect to the sample tube 80.

First, the on-off valve 42 is set to be in the on state and the on-off valves 46 and 48 are sequentially set to be in the on state. Thus, the helium gas is introduced into the manifold 30 from the helium gas source 22. All of the on-off valves 37 and 40 to 54 return to the off state at an appropriate time, and at this time, a pressure of the manifold 30 is detected by the pressure gauge 58. When the detected pressure is defined as $P_S$, a temperature and a pressure of the helium gas introduced into the manifold 30 are defined as a reference temperature $T_S$ and a pressure $P_S$, respectively, and a volume thereof is defined as a reference volume $V_S$.

Next, the on-off valve 50 is set to be in the on state and a pressure of the sample tube 80 and the manifold 30 is detected by the pressure gauge 58 or pressure gauge 60. The detected pressure is defined as PD. Since the sample tube 80 has a temperature of 77 K and the helium gas is not adsorbed onto the film formed body 90 as the sample even at a nitrogen adsorption temperature or lower, the helium gas introduced into the manifold 30 spreads over the manifold 30 and the sample tube 80. Therefore, the dead volume $V_D$ of the sample tube 80 in which the film formed body 90 is accommodated is calculated using a relational expression of $P_S V_S = P_D (V_S + V_D)$.

When the calculation of the dead volume $V_D$ is completed, the on-off valves 46 and 48 are sequentially set to be in the on state, and then the on-off valve 44 is set to be in the on state, whereby the exhaust pump 26 is actuated. Thus, the helium gas used in the calculation of the dead volume is exhausted to the outside from the sample tube 80. After the pressure of the sample tube 80 is sufficiently reduced to be in a state similar to a vacuum, all of the on-off valves 37 and 40 to 54 return to the off state, and the actuation of the turbo molecular pump 66 in the exhaust pump 26 stops. The above processing is also similarly executed with respect to the sample tube 82 to calculate the dead volume of the sample tube 82, and after the calculation, all of the on-off valves 37 and 40 to 54 return to the off state.

Next, the adsorption amount of the nitrogen gas as the adsorption gas onto the film formed body 90 is calculated based on the pressure P1 detected in the supply processing step 76 and the dead volume $V_D$ obtained by the dead volume calculating step. This processing step is executed by the function of the adsorption amount calculating step 78 in the measurement controller 70.

As described above, with respect to the description of the case in which the introduction processing step and the supply processing step may be repeatedly performed as a set of processing steps, for example, when the nitrogen gas is not totally adsorbed onto the film formed body 90 as the sample and the pressure $P_S$ equal to the pressure at the time of the calculation of the dead volume is introduced into the manifold 30 which is a reference volume portion in a first set of introduction processing step and supply processing step, the pressure P1 is equal to the pressure PD at the time of the calculation of the dead volume. Since the mole number "n" of an ideal gas is expressed as a relation of n=PV/RT when a pressure, a volume, a temperature, and a gas constant are defined as "P", "V", "T", and "R", respectively, the mole number nD of the nitrogen gas corresponding to the pressure at P1=PD is the mole number of the nitrogen gas in the manifold 30 and the sample tube 80, and is expressed by a relation of $n_D = \{P_D (V_S + V_D)\}/RT$. When the nitrogen gas is adsorbed onto the film formed body 90 which is the sample, the pressure P1 is a value $(P_D - P_A)$ lower than the pressure $P_D$ by the pressure $P_A$ depending on the adsorption amount. The pressure $(P_D - P_A)$ is a pressure of the nitrogen gas which remains in the sample tube 80 without being adsorbed onto the film formed body 90. The mole number nR of the residual nitrogen gas not being adsorbed satisfies the following formula: $n_R = \{(P_D - P_A)(V_S + V_D)\}/RT$.

For this reason, the mole number Δn of the nitrogen gas adsorbed on the film formed body 90 in the first set of steps described above satisfies the following formula: $\Delta n = (n_D - n_R) \{P_A(V_S + V_D)\}/RT$. Thus, the adsorption amount of the nitrogen gas adsorbed onto the film formed body 90 is calculated based on the ideal gas equation. However, since a real gas such as the nitrogen gas is not an ideal gas, a compression factor is used, or the correction as a non-ideal gas is performed, for example, in consideration of facts that the pressure in the low pressure portion is different due to a thermal transpiration phenomenon and the $V_D$ changes from moment to moment, whereby the accuracy in the calculation of the adsorption amount can be increased. In addition, the adsorption amount after the second set of steps is obtained in such a manner that the mole number remaining after equilibrium is subtracted from the sum of the mole number remaining in the dead volume portion of the sample tube 80 and the mole number introduced into the manifold 30 which is a reference volume portion.

Herein, the temperature of the dead volume over the entire length of the sample tube 80 has a mixed distribution of 77 K and a room temperature. In order to obtain the adsorption isotherm using the constant volume method, it is necessary to set the temperature of the film formed body 90 to the constant temperature of 77 K. As described in FIGS. 2A and 2B, it is possible to reduce the dead volume over the entire length of the sample tube 80 using the glass rod 94. Moreover, since the void between the inner wall surface of the sample tube 80 and the film formed body 90 is filled with the particle-like filler 92 having higher thermal conductivity, the temperature of the film formed body 90 can be set to 77 K. In addition, it is possible to reduce heat radiation from the sample-side region 93 and heat radiation from the glass rod 94 due to the action of the thermal insulation space 97 formed by the spacer ring 96 and the reflection plate 98. Furthermore, it is possible to perform a calibration of the sample tube 82 as a reference sample tube, which is disposed with the particle-like filler 92, the glass rod 94, the spacer ring 96, and the reflection plate 98 in the same manner as in the sample tube 80, for the lowering of the liquid level 13 of the refrigerant 12. Moreover, the saturated vapor pressure of the nitrogen gas is always detected using the saturated vapor pressure pipe 84. For this reason, it is possible to reduce the calculation error An when the temperature T is set to 77 K and calculate the adsorption amount with high accuracy.

Figure 4A:
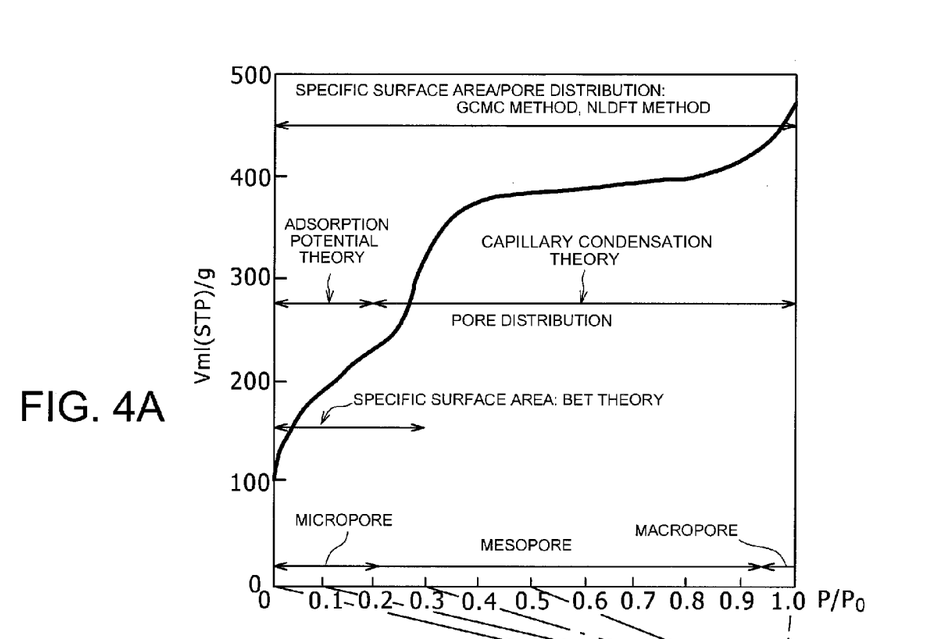
FIG. 4A is a diagram illustrating an example of an adsorption isotherm that is obtained by the adsorption characteristic measuring apparatus according to the embodiment of the invention, and is a general adsorption isotherm model.
Figure 4B:
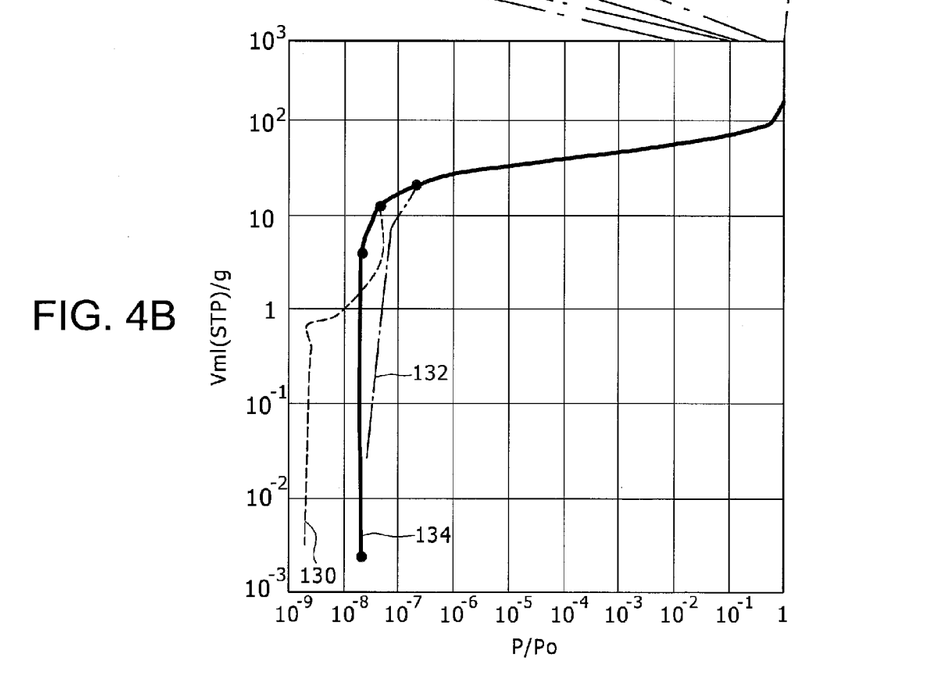
FIG. 4B is a diagram illustrating an example of an adsorption isotherm that is obtained by the adsorption characteristic measuring apparatus according to the embodiment of the invention, and is measured under very low relative pressure.

An adsorption isotherm measured using the adsorption characteristic measuring apparatus 10 attached with the sample tubes 80 and 82 having the above configuration will be described with reference to FIGS. 4A and 4B. FIG. 4A is a diagram illustrating a model of a general adsorption isotherm, and FIG. 4B illustrates an adsorption isotherm measured under a very low relative pressure. In FIGS. 4A and 4B, a horizontal axis indicates a relative pressure ($P/P_0$) obtained by normalization of the equilibrium pressure P of the adsorption gas with the saturated vapor pressure $P_0$ of the adsorption gas. A vertical axis indicates a value {V (ml: STP)/g} obtained by conversion of the adsorption amount into the volume of the adsorption gas in a standard state (STP) of 0° C. and 1 atm. Both of the vertical axis and the horizontal axis in FIG. 4A are indicated by actual numeric values, and both of the vertical axis and the horizontal axis in FIG. 4B are indicated by logarithmic values.

As illustrated in FIG. 4A, using measurement results of the adsorption isotherm, the evaluation of micropores can be performed in the range of the relative pressure ($P/P_0$) from 0 to 0.2, the evaluation of mesopores can be performed in the range of the relative pressure ($P/P_0$) from 0.2 to 0.95, and the evaluation of macropores can be performed in the range of the relative pressure ($P/P_0$) of more than 0.95. In addition, it is possible to apply a BET theory in the range of the relative pressure ($P/P_0$) from 0 to 0.3 and thus to calculate a specific surface area, using the measurement results of the adsorption isotherm. A pore distribution can be calculated using, for example, an SF method or an HK method based on an adsorption potential theory in the range of the relative pressure ($P/P_0$) from 0 to 0.2, and can be calculated using, for example, a BJH method or an INNES method based on a capillary condensation theory in the range of the relative pressure ($P/P_0$) from 0.2 to 1.0. Moreover, in recent years, the specific surface area and the pore distribution can be calculated using a GCMC method or an NLDFT method in the entire range of the relative pressure ($P/P_0$) from 0 to 1.0. Details of these theories and methods can be found in technical books and the description thereof will not be further presented.

FIG. 4B is a diagram illustrating adsorption isotherms 130, 132, and 134 measured under a very low relative pressure in which the relative pressure ($P/P_0$) is $10^{-6}$ or less. The adsorption isotherms 130 and 132 are results measured in the state where only the film formed body 90 is accommodated in the sample tube. As illustrated in FIG. 4B, variation in the measurement values was large and reproducibility was not obtained under a very low relative pressure where the relative pressure ($P/P_0$) is $3\times10^{-7}$ or less. The adsorption isotherm of the powder sample is measured depending on kinds of sample and kinds of adsorption gases, but reproducibility is ensured up to about $1\times10^{-8}$ under optimum conditions.

The adsorption isotherm 134 is a result measured in the state where the particle-like filler 92, the glass rod 94, the spacer ring 96, and the reflection plate 98 are disposed inside the sample tube 80 together with the film formed body 90 as illustrated in FIGS. 2A and 2B. As illustrated in FIG. 4B, variation in measurement values did not occur and excellent reproducibility was obtained up to a very low relative pressure in which the relative pressure ($P/P_0$) is $3\times10^{-8}$. Thus, even when the film formed body 90 was not formed into powder, it was possible to obtain the adsorption isotherm, which is appropriately comparable with the adsorption isotherm the optimum conditions of the powder, having excellent reproducibility in the form of the film formed body 90 even under the very low temperature.

What is claimed is:

1. An adsorption characteristic measuring apparatus that supplies a predetermined adsorption gas to a sample accommodated in a sample tube to measure an adsorption isotherm, the apparatus comprising:
   a refrigerant container that is filled with a constant temperature refrigerant having the sample tube immersed therein;
   a fitting portion that is provided at an opening of the sample tube;
   an adsorption gas supply portion that supplies the adsorption gas;
   a manifold that is connected via an on-off valve for the sample tube to the fitting portion;
   a manifold pressure gauge that detects a pressure of the manifold;
   a sample tube pressure gauge that detects an internal pressure of the sample tube; and
   a measurement controller that calculates the adsorption isotherm based on a change in the internal pressure of the sample tube, wherein
   the sample is a film formed body or a formed body, and
   a space between an inner wall surface of the sample tube and the sample is filled with a particle-like filler having higher thermal conductivity than the adsorption gas under a measurement pressure.

2. The adsorption characteristic measuring apparatus according to claim 1, wherein the particle-like filler is metal particles.

3. The adsorption characteristic measuring apparatus according to claim 2, wherein the particle-like filler is aluminum particles.

4. The adsorption characteristic measuring apparatus according to claim 1, wherein the inside of the sample tube is disposed with: a dead volume reducing rod that is made of the same material as the sample tube to reduce an upper dead volume of a sample-side region which is a region around the sample filled with the particle-like filler; and a spacer ring that is provided between a bottom side of the dead volume reducing rod and an upper surface side of the sample-side region and has lower thermal conductivity than the particle-like filler.

5. The adsorption characteristic measuring apparatus according to claim 4, further comprising a reflection plate that adheres to the bottom side of the dead volume reducing rod to reflect radiant heat from the sample-side region and the dead volume reducing rod.

6. The adsorption characteristic measuring apparatus according to claim 1, wherein the fitting portion is a joint that is used such that metal surfaces are airtightly held by being abutted against each other.

7. The adsorption characteristic measuring apparatus according to claim 1, wherein the film formed body is formed with a film having pores of different diameters, ranging from micropores to macropores, on a surface of a tubular support body, and wherein the formed body has pores of different diameters ranging from micropores to macropores.

* * * * *

UNITED STATES PATENT AND TRADEMARK OFFICE
CERTIFICATE OF CORRECTION

| | |
|---|---|
| PATENT NO. | : 9,645,069 B2 |
| APPLICATION NO. | : 14/853476 |
| DATED | : May 9, 2017 |
| INVENTOR(S) | : Matsukata et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 46 days.

Signed and Sealed this
Fifth Day of June, 2018

Andrei Iancu
*Director of the United States Patent and Trademark Office*